(12) United States Patent
Kari

(10) Patent No.: US 8,216,297 B2
(45) Date of Patent: Jul. 10, 2012

(54) DUAL CHAMBER CUFF STRUCTURE

(75) Inventor: Stuart E. Kari, Windsor, CA (US)

(73) Assignee: Trivascular, Inc., Santa Rosa, CA (US)

( * ) Notice: Subject to any disclaimer, the term of this patent is extended or adjusted under 35 U.S.C. 154(b) by 3 days.

(21) Appl. No.: 11/504,434

(22) Filed: Aug. 14, 2006

(65) Prior Publication Data

US 2008/0058920 A1    Mar. 6, 2008

(51) Int. Cl.
*A61F 2/06* (2006.01)

(52) U.S. Cl. .................................................. 623/1.25

(58) Field of Classification Search .................. None
See application file for complete search history.

(56) References Cited

U.S. PATENT DOCUMENTS

| | | | | |
|---|---|---|---|---|
| 4,637,394 A | * | 1/1987 | Racz et al. | 606/202 |
| 4,641,653 A | * | 2/1987 | Rockey | 606/194 |
| 5,156,620 A | | 10/1992 | Pigott | |
| 5,985,307 A | * | 11/1999 | Hanson et al. | 424/423 |
| 6,059,823 A | | 5/2000 | Holman et al. | |
| 6,129,758 A | * | 10/2000 | Love | 623/2.11 |
| 6,312,462 B1 | | 11/2001 | McDermott et al. | |
| 6,331,191 B1 | | 12/2001 | Chobotov | |
| 6,395,019 B2 | | 5/2002 | Chobotov | |
| 6,540,659 B1 | * | 4/2003 | Milbocker | 600/17 |
| 6,761,733 B2 | | 7/2004 | Chobotov et al. | |
| 6,776,604 B1 | | 8/2004 | Chobotov et al. | |
| 6,827,735 B2 | | 12/2004 | Greenberg | |
| 7,081,129 B2 | | 7/2006 | Chobotov | |
| 7,803,195 B2 | * | 9/2010 | Levy et al. | 623/23.68 |
| 2001/0023369 A1 | | 9/2001 | Chobotov | |
| 2002/0169497 A1 | * | 11/2002 | Wholey et al. | 623/1.13 |
| 2003/0120338 A1 | | 6/2003 | Chobotov et al. | |
| 2003/0125797 A1 | | 7/2003 | Chobotov et al. | |
| 2003/0176911 A1 | | 9/2003 | Iancea et al. | |
| 2003/0216802 A1 | | 11/2003 | Chobotov | |
| 2003/0225453 A1 | | 12/2003 | Murch | |
| 2004/0138734 A1 | | 7/2004 | Chobotov et al. | |

(Continued)

FOREIGN PATENT DOCUMENTS

WO    2006073972    7/2006

OTHER PUBLICATIONS

C. Donayre, et al., "Fillable endovascular aneurysm repair", Endovascular Today, pp. 64-66, Jan. 2009.

*Primary Examiner* — Thomas J Sweet
*Assistant Examiner* — Rebecca Straszheim
(74) *Attorney, Agent, or Firm* — Hoffmann & Baron, LLP

(57) ABSTRACT

The endovascular graft includes a dual chamber cuff structure. The endovascular graft includes a tubular structure having a first end and a second end. The tubular structure has a wall defining a lumen between the first and second ends. The endovascular graft includes a cuff circumferentially secured to the tubular structure. The cuff has an interior cavity which is bifurcated such that the interior cavity includes a circumferential outer chamber and a circumferential inner chamber. The method for forming the endovascular graft includes inserting an expansion substance into the inner chamber to resist a luminal intrusion of the tubular structure resulting from the insertion of the expansion substance into the outer chamber. The expansion substance within the outer chamber is stiffened. The expansion substance within the inner chamber is removed.

11 Claims, 4 Drawing Sheets

U.S. PATENT DOCUMENTS

| | | |
|---|---|---|
| 2004/0176836 A1* | 9/2004 | Kari et al. .................... 623/1.32 |
| 2005/0090804 A1 | 4/2005 | Chobotov et al. |
| 2005/0154444 A1 | 7/2005 | Quadri |
| 2005/0171593 A1* | 8/2005 | Whirley et al. .............. 623/1.13 |
| 2005/0228484 A1 | 10/2005 | Stephens et al. |
| 2005/0240075 A1* | 10/2005 | Li .................................. 600/30 |
| 2006/0025853 A1 | 2/2006 | Evans et al. |
| 2006/0178732 A1 | 8/2006 | Chobotov et al. |
| 2006/0212112 A1 | 9/2006 | Evans et al. |
| 2006/0292206 A1* | 12/2006 | Kim et al. .................... 424/443 |

* cited by examiner

DUAL CHAMBER CUFF STRUCTURE

FIELD OF THE INVENTION

The present invention relates generally to an expandable cuff for an endovascular graft, and a method for forming the same. More specifically, the present invention relates to an expandable cuff which has two chambers to limit luminal intrusion of the cuff within the graft.

BACKGROUND OF THE INVENTION

Endovascular grafts are known for treating disorders of the vasculature. Such endovascular grafts may include a tubular structure and one or more circumferential cuffs secured thereto. Such circumferential cuffs may be near the proximal or distal ends of the tubular structure. The cuffs may be expandable, which allows the cuffs to have a non-expanded condition in which the cuffs have a reduced diameter and profile. Such a reduced diameter and profile of the cuffs facilitates deployment thereof and the tubular structure into and through the vasculature of the patient by a delivery system, such as may include a catheter. Following the completion of the positioning of the endovascular graft within the vasculature of the patient, the cuffs may be expanded to provide support to the tubular structure and to seal the graft against the inner surface of the vasculature in which the graft is deployed. The cuffs may be expanded by inflation, such as by providing to the interior of the cuffs a pressurized source of gas, fluid, particles, gel or a combination thereof. Examples of such an endovascular graft are disclosed in U.S. Pat. No. 6,395,019 and U.S. Patent Application Publication No. US 2003/0120338 which are hereby incorporated by reference herein.

Expansion of the cuffs typically results in displacement of the cuffs which is both luminal and abluminal relative to the tubular structure to which the cuffs are secured. Abluminal expansion refers to expansion of the cuffs in a radially outward direction beyond the outer surface of the tubular structure. Luminal expansion refers to expansion of the cuffs in a radially inward direction from the inner surface of the tubular structure into the lumen thereof. The luminal and abluminal expansions of the cuffs results in the expansion thereof being generally symmetrical relative to the wall of the tubular structure. The abluminal expansion of the cuffs may appear to resemble a bulge extending from the outer surface of the tubular structure. The luminal expansion of the cuffs may appear to resemble a bulge extending from the inner surface of the tubular structure.

The luminal expansion of the cuffs typically reduces the cross-sectional area of the lumen of the tubular structure in the axial region of the cuff. Such a reduction in the cross-sectional area of the lumen may provide a restriction to the fluid flow within the lumen. Such a restriction may result in an increased pressure of, turbulence in, or other characteristics of the fluid within the lumen which are frequently desired to be substantially limited or non-existent. Consequently, it is typically desirable for the cuffs to have little or no luminal expansion relative to the tubular structure. Expansion of the cuff is nevertheless desired to obtain the benefits thereof, which include the structural support of the tubular structure and the improved sealing thereof against the inner surface of the vasculature.

SUMMARY OF THE INVENTION

The endovascular graft of the present invention includes a dual chamber cuff structure. The endovascular graft includes a tubular structure having a first end and a second end. The tubular structure has a wall defining a lumen between the first and second ends. The endovascular graft includes a cuff circumferentially secured to the tubular structure. The cuff has an interior cavity which is bifurcated such that the interior cavity includes a circumferential outer chamber and a circumferential inner chamber.

The method for forming the endovascular graft of the present invention includes inserting an expansion substance into the outer chamber. An expansion substance is inserted into the inner chamber such that a luminal intrusion of the tubular structure resulting from the insertion of the expansion substance into the outer chamber is resisted by the insertion of the expansion substance within the inner chamber. Consequently, the expansion of the outer chamber results in an insubstantial or no reduction in the cross-sectional area of the lumen of the tubular structure and associated flow restriction therein.

The expansion substance within the outer chamber is stiffened. The expansion substance within the inner chamber is removed. The stiffening of the expansion substance within the outer chamber provides for the expansion thereof to remain following the completion of the implantation of the graft in the patient. Consequently, the stiffened expansion substance within the outer chamber provides support to the graft and sealing thereof against the inner surface of the vasculature.

The flexibility of the annular portion of the wall of the tubular structure facilitates the collapse of inner chamber against the intermediate layer when the expansion substance is removed from the inner chamber. The collapse of the inner chamber substantially reduces or eliminates completely luminal intrusion of the annular portion. Consequently, the collapsed inner chamber results in an insubstantial or no reduction in the cross sectional area of the lumen of the tubular structure and associated flow restriction therein.

These and other features of the invention will be more fully understood from the following description of specific embodiments of the invention taken together with the accompanying drawings.

DETAILED DESCRIPTION OF THE INVENTION

Figure 1:
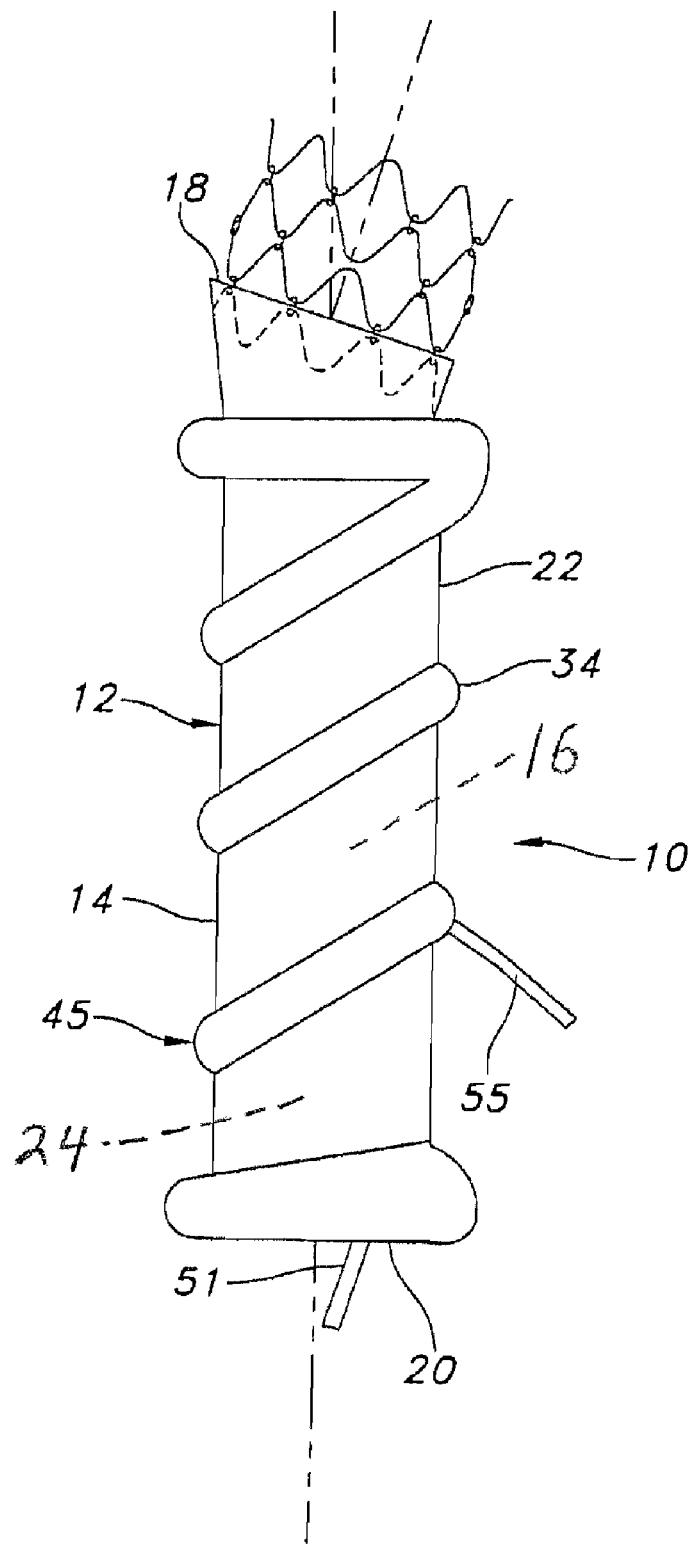
FIG. 1 is a perspective view of an endovascular graft in accordance with the present invention, the endovascular graft being shown as having outer chamber which is expanded by an expansion substance contained therein.
Figure 2:
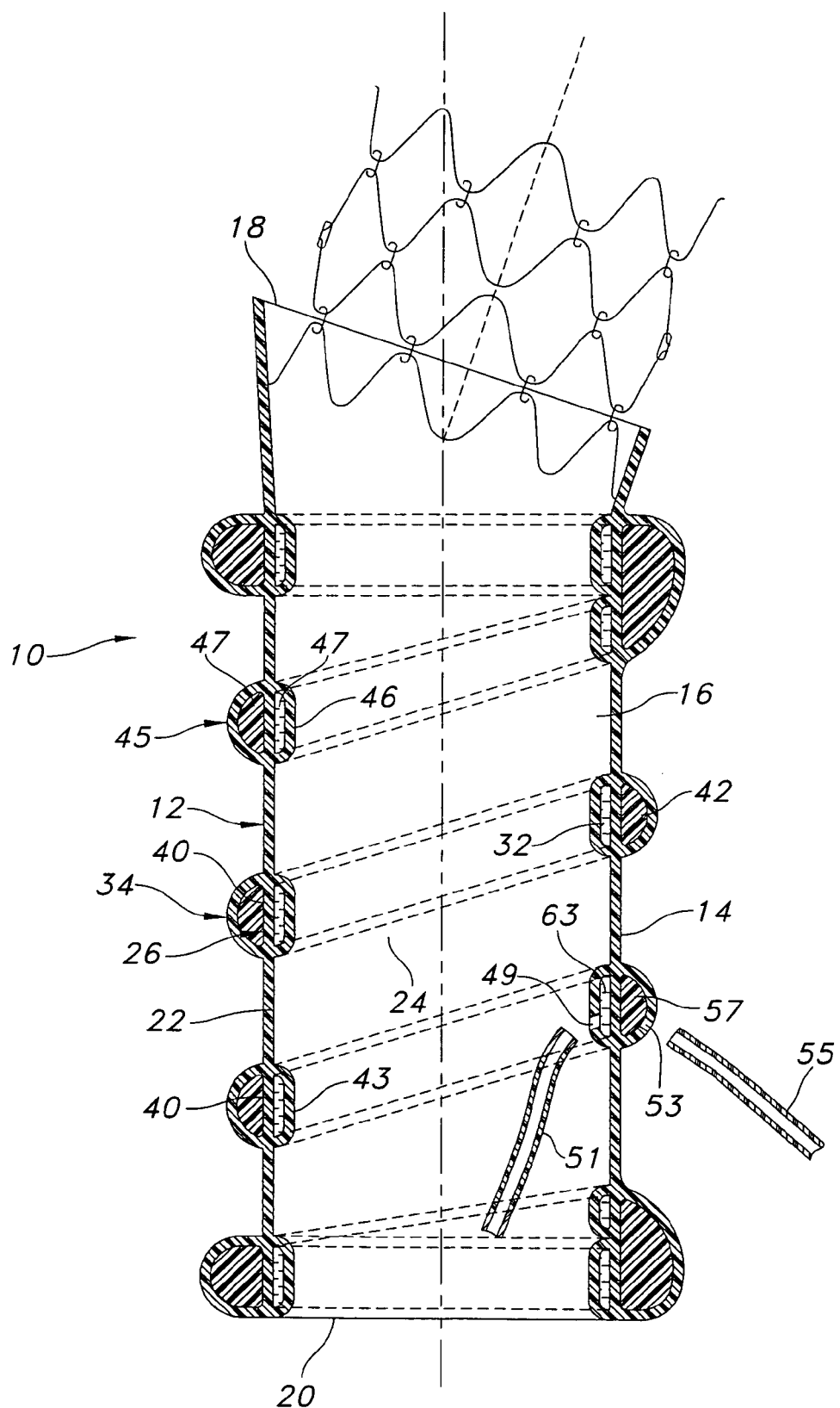
FIG. 2 is a longitudinal cross sectional view in perspective of the endovascular graft of FIG. 1, the endovascular graft being shown as having outer and inner chambers, the outer chamber being illustrated as expanded by an expansion substance contained therein, the inner chamber being shown as collapsed from the removal of the expansion substance previously contained therein, the endovascular graft being illustrated as located within an elongate vessel.

Referring to the drawings, wherein like reference characters designate corresponding parts throughout all of the figures, the endovascular graft 10 includes a tubular structure 12 having an outer surface 14 and an inner surface 16 (see, e.g. FIGS. 1 and 2). The tubular structure 12 has a first end 18 and a second end 20. The tubular structure 12 has a wall 22 which defines a lumen 24 between the first and second ends 18, 20.

Figure 3:
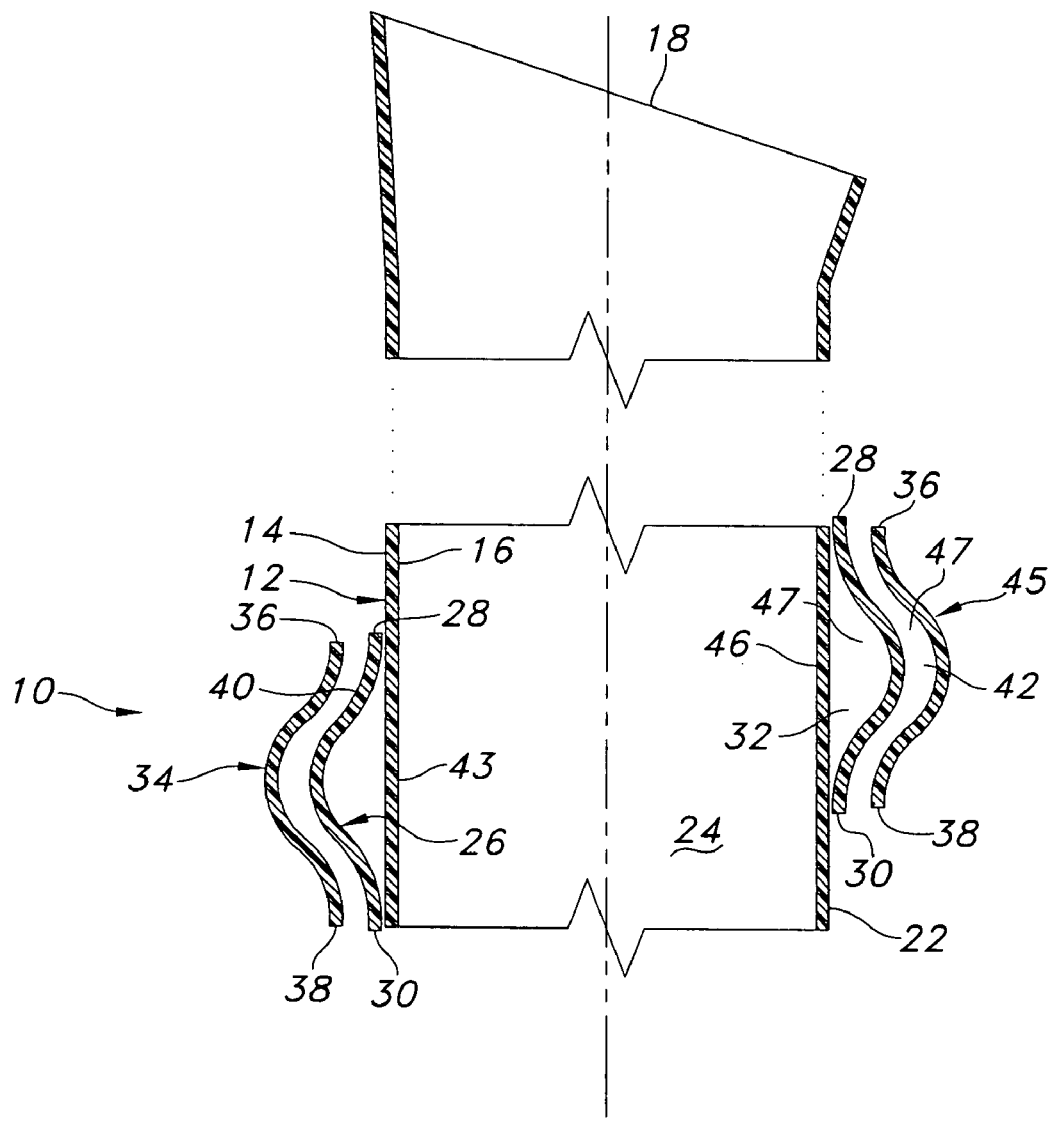
FIG. 3 is a longitudinal cross sectional view of the endovascular graft of FIG. 1, the endovascular graft being shown before the expansion of the outer and inner chambers by the expansion substance therein.

The endovascular graft 10 includes an elongate circumferential intermediate layer 26 which has a first transverse edge 28 and a second transverse edge 30, as shown in FIG. 3. The first and second transverse edges 28, 30 are attached to the outer surface 14 such that a circumferential inner chamber 32 is defined between the outer surface and intermediate layer 26. The tubular structure 12 has an annular portion 43 the outer surface of which coincides with the section of the outer surface 14 which constitutes a portion of the enclosure of the inner chamber 32.

The endovascular graft 10 includes an elongate circumferential outer layer 34 which has a first transverse edge 36 and a second transverse edge 38, as shown in FIG. 3. The first and second transverse edges 36, 38 are attached to the outer surface 40 of the intermediate layer 26 or to the outer surface 14 of the tubular structure 12. This attachment defines a circumferential outer chamber 42 between the outer layer 34 and intermediate layer 26.

The intermediate and outer layers 26, 34, and annular portion 43 define a cuff 45 which is circumferentially secured to the tubular structure 12. The annular portion 43 defines an inner layer 46 of the cuff 45. The inner and outer chambers 32, 42 define an interior cavity 47 of the cuff 45. The interior cavity 47 is bifurcated by the intermediate layer 26. Consequently, the interior cavity 47 includes the inner and outer chambers 32, 42.

Figure 4:
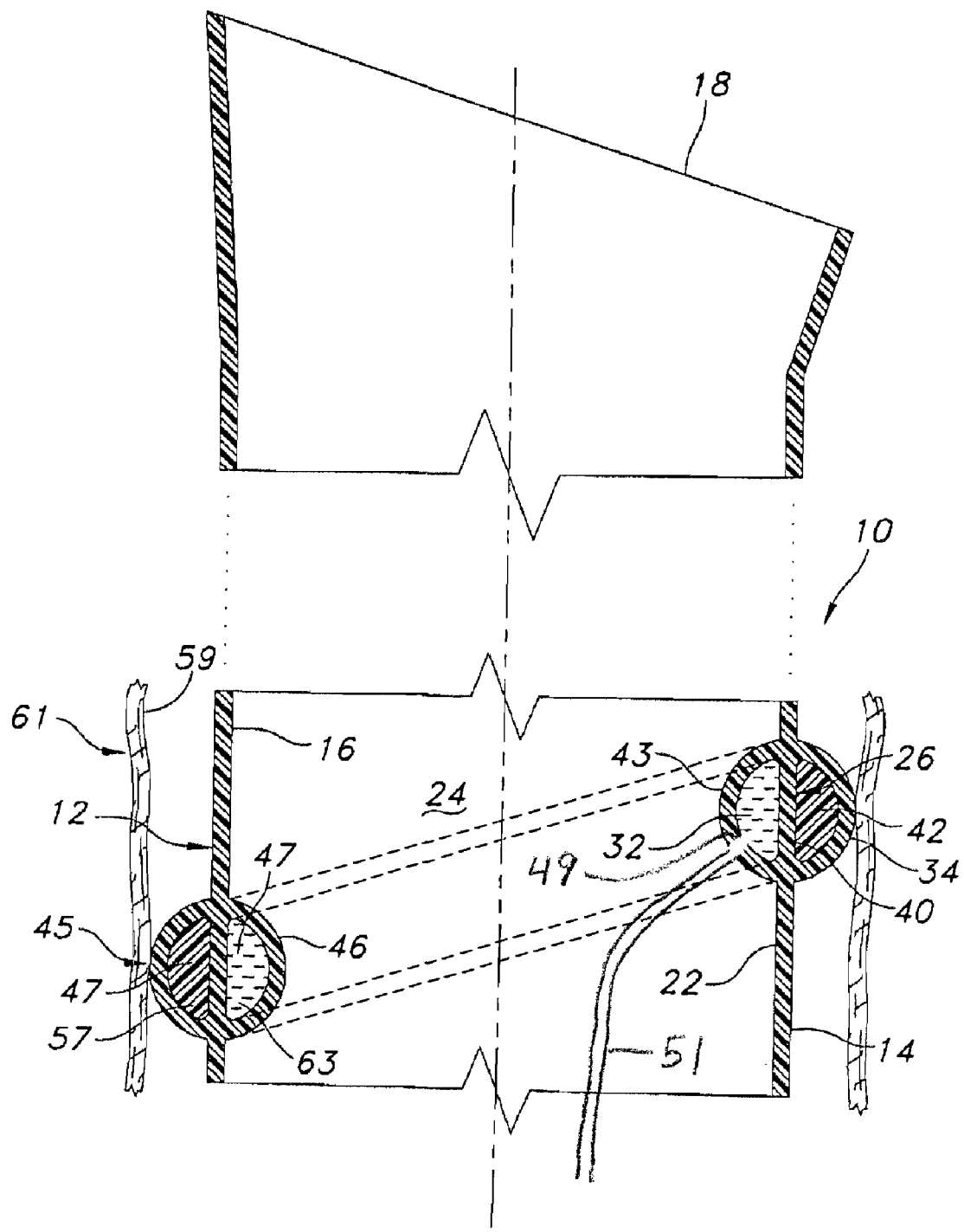
FIG. 4 is a longitudinal cross sectional view in perspective of the endovascular graft of FIG. 1, the endovascular graft being shown as having outer and inner chambers each of which is expanded by a respective expansion substance contained therein, the endovascular graft being illustrated as located within an elongate vessel.

The annular portion 43 has a flexibility for radial displacement relative to the adjoining portions of the wall 22. This flexibility provides for variation in the volume of the inner chamber 32, as shown in FIGS. 2 and 4.

The endovascular graft 10 has a port 49 which extends through the annular portion 43. The port 49 provides communication between the inner chamber 32 and a conduit 51. The conduit 51 extends to a location which is external to the cuff 45 and tubular structure 12.

The endovascular graft 10 has a port 53 which extends through the outer layer 34. The port 53 provides communication between the outer chamber 42 and a conduit 55 which is located externally of the cuff 45 and tubular structure 12.

The endovascular graft 10 has an expansion substance 57 within the outer chamber 42. The expansion substance 57 within the outer chamber 42 provides support to the tubular structure 12 and seals the endovascular graft 10 against the interior surface 59 of the vessel 61 in which the graft is deployed, as shown in FIG. 4. The expansion substance 57 is a polymer. Other materials may be included in the expansion substance 57 in alternative embodiments thereof.

The inner chamber 32 of the completely formed endovascular graft 10 is substantially empty, as shown in FIG. 2. This substantially reduces or eliminates completely luminal intrusion into the lumen 24 of the section of the inner surface 16 which coincides with the inner surface of the inner layer 46. This results in an insubstantial or no reduction in the cross sectional area of the lumen 24 and associated flow restriction therein.

The formation of the endovascular graft 10, including the substantially empty inner chamber 32 and the expansion substance 57 in the outer chamber 42, is provided by a method which includes inserting the expansion substance 57 into the outer chamber 42, as shown in FIG. 4. This insertion may be provided by an expansion substance which is a polymer having sufficient flexibility to flow through the conduit 55 and the port 53 into the outer chamber 42.

An expansion substance 63 is inserted into the inner chamber 32 to provide resistance to luminal intrusion of the annular portion 43 or inner layer 46 which may result from the insertion of the expansion substance 57 into the outer chamber 42, as shown in FIG. 4. The insertion of the expansion substance 63 into the inner chamber 32 may be provided by the expansion substance having a sufficient flexibility to flow through the conduit 51 and port 49 into the inner chamber. This flexibility may be provided by the expansion substance 63 being a fluid such as a saline solution. The insertion of the expansion substance 63 into the inner chamber 32 may be substantially simultaneous with the insertion of the expansion substance 57 into the outer chamber 42.

After the insertions of the expansion substances 57, 63 into the outer and inner chambers 42, 32, the expansion substance 57 is stiffened. The stiffening may be provided by the expansion substance 57 being a polymer which may be cured to increase the stiffness thereof. The stiffening of the expansion substance 57, which is such a polymer, is provided by curing the polymer following the insertion thereof into the outer chamber 42.

After the expansion substance 57 in the outer chamber 42 has been stiffened, the expansion substance 63 which is within the inner chamber 32 is removed therefrom, as shown in FIG. 2. This removal of the expansion substance 63 may be provided by the flow of the expansion substance 63 through the port 49 and conduit 51. Alternatively, the expansion substance 63 may be removed from the inner chamber 32 by having the annular portion 43 or inner layer 46 be a material which is permeable. This permeability of the annular portion 43 provides for an osmotic flow of the expansion substance 63 from within the inner chamber 32 luminally through the annular portion 43 into the lumen 24. Removal of the expansion substance 63 from the inner chamber 32 substantially reduces or eliminates completely luminal intrusion of the annular portion 43.

The first end 18 of the tubular structure 12 defines an upstream end through which the fluid, typically blood, enters the lumen 24. A cuff 45 may be located longitudinally relative to the tubular structure 12 such that the cuff is adjacent to the upstream or first end 18, as shown in FIGS. 1 and 2. The second end 20 of the tubular structure 12 defines a downstream end through which the fluid which is within the lumen 24 exits therefrom. The cuff 45 may be located longitudinally relative to the tubular structure 12 such that the cuff is adjacent to the downstream or second end 20, as shown in FIGS. 1 and 2.

The ports 49, 53 may be located relative to the tubular structure 12 such that insertion of the endovascular graft 10 through an ipsilateral location on the body of the patient provides for the ports to have a contralateral position relative to the body of the patient. Consequently, the conduits 51, 55 shown in FIGS. 1 and 2 may extend through a section of the body of the patient which is different from the section thereof through which the endovascular graft 10 is inserted.

While the invention has been described by reference to certain preferred embodiments, it should be understood that numerous changes could be made within the spirit and scope of the inventive concept described. Accordingly, it is intended that the invention not be limited to the disclosed embodiments, but that it have the full scope permitted by the language of the following claims.

What is claimed is:

1. An endovascular graft comprising:
   a tubular structure having a first end and a second end, said tubular structure having a wall defining a lumen between said first and second ends, said tubular structure having an outer surface and an inner surface;
   a circumferential cuff, said cuff comprising an interior cavity which is bifurcated such that said interior cavity comprises a circumferential outer chamber and a circumferential inner chamber;
   an elongate circumferential intermediate layer having a transverse first edge and a transverse second edge which are attached to said outer surface of said tubular structure such that said inner chamber is defined between an annular portion of said outer surface of said tubular structure and said intermediate layer; and
   an elongate circumferential outer layer having a transverse first edge and a transverse second edge which are attached to an outer surface of said intermediate layer or said outer surface of said tubular structure such that said outer chamber is defined between said outer layer and said intermediate layer;
   wherein said outer chamber comprises a stiffened expansion substance following completion of the implantation of the graft in a patient;
   wherein said inner chamber comprises a fluid during implantation of the graft in the patient such that the inner chamber expands into the lumen, and wherein said fluid is configured to be removed from the inner chamber prior to the completion of the implantation of the graft in the patient such that the inner chamber assumes a collapsed state which results in an insubstantial or no reduction in a cross sectional area of the lumen of the tubular structure.

2. An endovascular graft according to claim 1, said annular portion having a flexibility for radial displacement relative to an adjoining portion of said wall to provide for variation in a volume of said inner chamber.

3. An endovascular graft according to claim 1, wherein said fluid comprises a saline solution.

4. An endovascular graft according to claim 1, further comprising a port.

5. An endovascular graft according to claim 4, wherein said port extends through the circumferential outer layer.

6. An endovascular graft according to claim 5, wherein said port provides communication between said outer chamber and a conduit located external of said cuff and said tubular structure.

7. The graft of claim 4, wherein said port extends through the annular portion.

8. An endovascular graft according to claim 7, wherein said port provides communication between said inner chamber and a conduit which extends to a location which is external to said cuff and said tubular structure.

9. An endovascular graft according to claim 1, wherein said expansion substance comprises a polymer.

10. An endovascular graft according to claim 1, wherein said first end of said tubular structure defines an upstream end, said cuff being adjacent to said upstream end.

11. An endovascular graft according to claim 1, wherein said second end of said tubular structure defines a downstream end, said cuff being adjacent to said downstream end.

* * * * *